United States Patent [19]

Eibl

[11] Patent Number: 5,436,234
[45] Date of Patent: Jul. 25, 1995

[54] EURCYL, BRASSIDYL AND NERVONYL DERIVATIVES

[75] Inventor: Hansjörg Eibl, Bovenden-Eddiegehausen, Germany

[73] Assignee: Max-Planck-Gesellschaft zur Förderung, Götingen, Germany

[21] Appl. No.: 203,618

[22] Filed: Feb. 28, 1994

Related U.S. Application Data

[63] Continuation of Ser. No. 862,627, Apr. 1, 1992, abandoned.

[30] Foreign Application Priority Data

Apr. 5, 1991 [DE] Germany .......................... 41 11 105.2

[51] Int. Cl.$^6$ ...................... A61K 31/685; C07F 9/10
[52] U.S. Cl. ........................................ 514/77; 558/169
[58] Field of Search ........................... 514/77; 558/169

[56] References Cited

U.S. PATENT DOCUMENTS

| | | | |
|---|---|---|---|
| 4,542,219 | 9/1985 | Hozumi et al. | 546/22 |
| 4,562,005 | 12/1985 | Nojima et al. | 260/403 |
| 5,049,552 | 9/1991 | Eibl | 514/77 |

FOREIGN PATENT DOCUMENTS

| | | |
|---|---|---|
| 0061872 | 10/1982 | European Pat. Off. . |
| 0108565 | 5/1984 | European Pat. Off. . |

OTHER PUBLICATIONS

Kötting et al., Cancer Chemotherapy and Pharmacology, vol. 30, No. 2, 1992, pp. 105–112.

*Primary Examiner*—Robert W. Ramsuer
*Assistant Examiner*—Michael G. Ambrose
*Attorney, Agent, or Firm*—Nikaido, Marmelstein, Murray & Oram

[57] ABSTRACT

The present invention provides compounds of the formula:

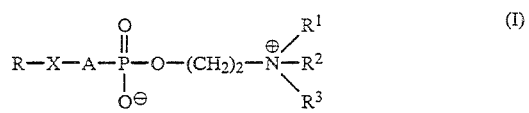

wherein R is a erucyl, brassidyl or nervonyl radical, $R^1$, $R^2$ and $R^3$ are defined in the specification, A is a valency bond or a radical as defined in the specification, and X is an oxygen atom when A is a valency bond or is an oxygen or sulphur atom when A is another radical.

The present invention also provides a process for the preparation of the compounds of general formula (I) and pharmaceutical compositions containing them which can be used for the treatment of protozoal and fungal diseases, auto-immune diseases and bone marrow damage.

12 Claims, No Drawings

EURCYL, BRASSIDYL AND NERVONYL DERIVATIVES

This application is a continuation of application of Ser. No. 07/862,627 filed Apr. 1, 1992, abandoned.

The present invention is concerned with new phospholipids which contain a erucyl, brassidyl or nervonyl radical and with the use thereof as medicaments, especially for combatting tumours, as well as protozoal and fungal diseases and also for the therapy of autoimmune diseases and damage to the bone marrow.

The use of phospholipids as medicaments is known. EP-A-0 108 565 discloses phospholipids, as well as the pharmaceutically acceptable salts thereof, of the general formula:

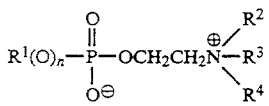

where $R^1$ is an aliphatic $C_8$-$C_{30}$-hydrocarbon radical, $R^2$, $R^3$ and $R^4$, independently of one another, are hydrogen atoms or $C_1$-$C_5$-alkyl radicals or wherein

represents a cyclic ammonium radical and n is 0 or 1. $R^1$ is preferably an aliphatic hydrocarbon radical with 12 to 22 and especially with 14, 17 or 18 carbon atoms. These compounds are especially suitable for combatting tumour cells and fungal diseases and for use as plant protective agents.

DE-OS-32 39 817 discloses glycerol derivatives of the general formula:

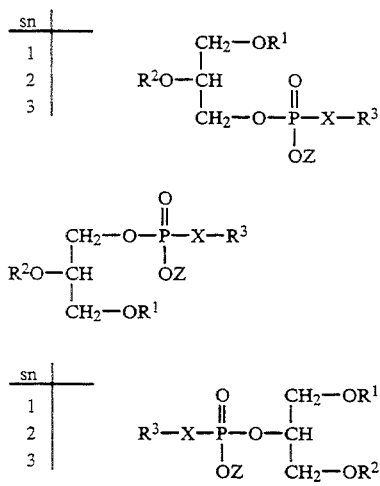

wherein $R^1$ and $R^2$ can be, inter alia, substituted or unsubstituted alkyl radicals containing up to 24 carbon atoms, X can be, inter alia, an oxygen atom and $R^3$ can be, inter alia, an aminoalkyl radical or an N-alkylaminoalkyl radical containing 2 to 14 carbon atoms in the alkyl radicals. Furthermore, there are also disclosed general processes for the preparation of the above compounds so that it is possible to prepare position-specifically glycerol derivatives with different radicals and with high specificity.

DE-OS-36 41 379 disclosed compounds of the general formula:

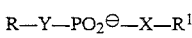

$$R-Y-PO_2^\ominus-X-R^1$$

wherein R can be a hydrocarbon radical containing 12 to 24 carbon atoms, X is, inter alia, an oxygen atom and $R^1$ can be, inter alia, an alkyl radical which can be substituted with different amino groups. R is preferably an alkyl or alkylene radical containing 14 to 20 carbon atoms, X is an oxygen atom and $R^1$ is a trialkylammonium ethyl radical with up to 3 carbon atoms in each alkyl moiety. The compounds hexadecylphosphocholine and oleylphosphocholine are especially preferred. Furthermore, there is disclosed the use of the above compounds as medicaments, especially for the treatment of tumours. For the topical treatment of skin tumours, such medicaments can also contain alkylglycerols as additional active materials. General methods of preparation for the compounds of the above-given general formula are also disclosed.

DE-OS-36 41 491 disclosed an antitumour-effective medicament which contains hexadecylphosphocholine as active material, as well as possibly further conventional additive, carrier and/or diluent materials. As additional active material, such a medicament can also contain an alkyl glycerol.

Furthermore, it is known that a glycerol derivative of hexadecylphosphocholine methylated in the 2-position, i.e. the ether phospholipid ET-18-OCH$_3$, is a very effective anti-tumour agent (see, for example Berdel et al. in Phospholipids and Cellular Regulation, 1985, published by J. F. Kuo, pages 41–74, CRC Press, Boca Raton, Fla., U.S.A.). In addition, ET-18OCH$_3$ has also proved to be a suitable medicament for combatting autoimmune diseases, for example multiple sclerosis.

From the above-mentioned publications, it can be seen that phosphatidylamines and ether lysolecithins are suitable as medicaments for various uses, for example for combatting tumours and auto-immune diseases. Hitherto, hexadecylphosphocholine and ET-18OOCH$_3$ have proved to be the most effective medicaments from this class of compounds. However, these compounds have the disadvantage that they show a toxic effect at high dosages. A further disadvantage of the previously known phospholipids is that they bring about a cytolysis of cells and especially a haemolysis of erythrocytes. Therefore, these compounds cannot be administered intravenously since this leads to haemolytic and tissue-necrotic accompanying phenomena, as is described in detail in DE 40 26 136.

Therefore, it is an object of the present invention to provide new phospholipids which are effective as medicaments but in the case of which the disadvantages of the prior art are at least partly overcome.

Thus, according to the present invention, there are provided compounds of the general formula:

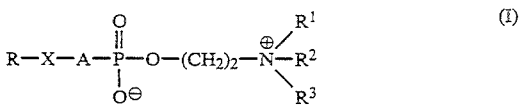

wherein R is a erucyl, brassidyl or nervonyl radical, $R^1$, $R^2$ and $R^3$ are, independently of one another, straight-chained, branched or cyclic saturated or unsaturated alkyl radicals containing up to 4 carbon atoms, which can also contain a hydroxyl group, and wherein two of these radicals can also be connected together to form a ring, A is a valency bond or a radical of one of the formulae:

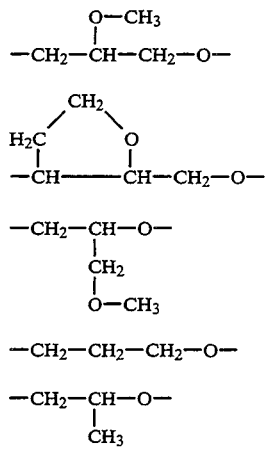

$$-CH_2-CH-CH_2-O- \quad (II)$$
$$\phantom{-CH_2-CH-CH_2-}|$$
$$\phantom{-CH_2-CH-CH_2-}O-CH_3$$

(III)

$$-CH_2-CH-O- \quad (IV)$$
$$\phantom{-CH_2-}|$$
$$\phantom{-CH_2-}CH_2$$
$$\phantom{-CH_2-}|$$
$$\phantom{-CH_2-}O-CH_3$$

$$-CH_2-CH_2-CH_2-O- \quad (V)$$

$$-CH_2-CH-O- \quad (VI)$$
$$\phantom{-CH_2-}|$$
$$\phantom{-CH_2-}CH_3$$

or $$-CH_2-CH_2-O- \quad (VII)$$

whereby the radicals (II) to (VII) have an orientation such that the oxygen atom is attached to the phosphorus atom of the compound (I), and X is an oxygen atom when A is a a valency bond or is an oxygen or sulphur atoms when A is one of the radicals (II) to (VII).

In the above general formula (I), X is preferably an oxygen atom and A is preferably a valency bond. It is also preferred that $R^1$, $R^2$ and $R^3$ are each methyl radicals so that the resulting compounds are phosphocholine derivatives, erucylphosphocholine being especially preferred.

Erucyl, brassidyl and nervonyl radicals are long-chained alkyl radicals. They can be obtained from the corresponding fatty acids, some of which occur naturally. Erucic acid (cis-13-docosenoic acid) occurs as the glycerol ester in mustard, grape seed, cod liver and Cruciferae oils and especially in rape seed oil. Brassidic acid (trans-13-docosenoic acid) stereoisomeric thereto does not occur naturally but can be obtained from erucic acid by heating with nitrous acid. Nervonic acid (selacholeic acid, cis-15-tetracosenoic acid) occurs in shark liver oils, sphingomyelins and cerebrosides and especially in nervone.

For the preparation of the compounds according to the present invention, fatty acids of the general formula:

$$R-COOH \quad (VIII)$$

in which R is an erucyl, brassidyl or nervonyl radical, can be converted by reduction according to known methods, preferably with lithium aluminium hydride, into the corresponding alcohols of the general formula:

$$R-OH \quad (IX)$$

These alcohols can then be converted into compounds according to the present invention also by means of known processes.

The preparation of compounds according to the present invention of general formula (I), in which X is an oxygen atom and A is a valency bond, can be carried out, for example, according to the processes described in DE 27 52 125, EP-A 0 108 565, DE 36 41 491, DE 36 41 379, DE 36 41 377 and DE 40 13 532 or according to the literature cited therein.

Preferably, the alcohol R—OH, in which R is a erucyl, brassidyl or nervonyl radical, is thereby converted directly by phosphorylation into the corresponding alkylphosphoamine derivative and especially into the corresponding alkylphosphocholine. For this purpose, for example, the alcohol of the general formula (IX) is reacted with a compound of the general formula:

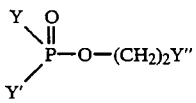 (X)

wherein Y, Y' and Y" are halogen atoms, for example the compound of general formula (X) can be 2-bromoethylphosphorus dichloride. From this reaction and subsequent working up by hydrolysis, there results a compound of the general formula:

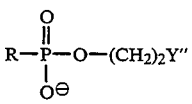 (XI)

in which R and Y" have the above-given meanings. The last step of the reaction includes the reaction of this compound of general formula (XI) with an amine of the general formula:

or with a quaternary ammonium salt of the general formula:

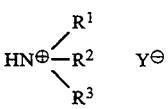

wherein $R^1$, $R^2$ and $R^3$ have the above-given meanings and Y is an appropriate anion. Examples of tertiary amines which can be used according to the present invention include trimethylamine, dimethylethylamine, diethylmethylamine, triethylamine, N,N, dimethyl-N-propylamine, N,N-dimethyl-N-isopropylamine, N-cyclopropyl-N,N-dimethylamine, N-allyl-N,N-dimethylamine, N-ethyl-N-methyl-N-propylamine, N-butyl-N,N-dimethylamine, N,N-dimethyl-N-hydroxyethylamine, N,N-dihydroxylethyl-N-methylamine, N-cyclobutyl-N,N-dimethylamine, N-methylpyrrolidine, N-ethylpyrrolidine, N-methylmorpholine and the like.

On the other hand, for the preparation of the compounds according to the present invention, the alcohols of general formula (IX) can be reacted with phosphorus oxychloride (POCl₃). After subsequent hydrolysis, there is obtained a compound of the general formula:

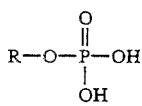
(XII)

This compound can in turn be reacted with a tertiary ammonium salt of the general formula:

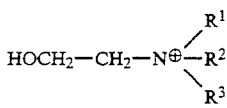

to give a compound of general formula (I) according to the present invention. The detailed reaction conditions are thereby to be found in the above-mentioned literature references.

The preferred process for the preparation of the compounds according to the present invention is the reaction of the alcohol of general formula (IX) with phosphorus oxychloride with the formation of the corresponding phosphoric acid dichloride of the general formula:

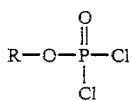
(XIII)

This compound is reacted with ethanolamine or with an appropriately substituted ethanolamine to give a heterocyclic, five-membered ring-containing compound of the general formula:

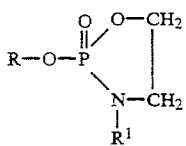
(XIV)

in which R has the above-given meaning and $R^1$ is a hydrogen atom or a methyl, ethyl or like radical. Opening of the ring under acidic conditions gives the corresponding phosphoethanolamine which, by alkylation, can be converted into the desired peralkylated compound of general formula (I), inter alia into phosphocholine. This process is described in detail by H. Eibl in Proc. Natl. Acad. Sci. U.S.A., 75, 4074–4077/1988.

The preparation of compounds of general formula (I) according to the present invention in which A is a group of the formula:

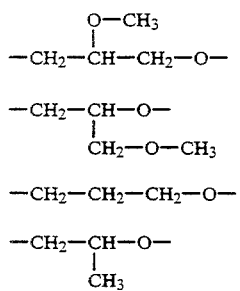

or $-CH_2-CH_2-O-$ (VII)

also takes place according to known processes. Besides the above-mentioned methods, an example herefor is given especially in DE 32 39 817. Furthermore, the alcohols of general formula (IX) can also be converted via the mesylates thereof into the corresponding alkylglycerols or into other derivatives, the phosphorylation of which then leads to the compounds according to the present invention.

The preparation of compounds in which X is a sulphur atoms can also take place according to the methods described by Bosies et al. (Lipids, 22, 947–951/1987) by a multi-step reaction from glycerol and a thiol of the general formula:

R—SH (XV)

in which R is an erucyl, brassidyl or nervonyl radical. On the other hand, the phosphorylation of the thiol can also take place by means of the above mentioned methods of phosphorylation.

The preparation of compounds of general formula (I) in which A is a radical of the formula:

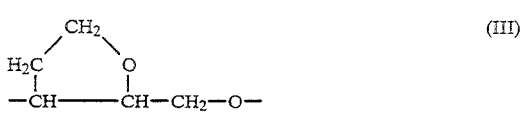
(III)

takes place according to the method described by Houlihan et al (Lipids, 22, 884–890/1987) starting from the commercially available 2-furancarboxylic acid. On the other hand, the alcohol can, as base material, also be phosphorylated according to the above-mentioned methods and then further reacted.

The compounds according to the present invention have proved to be highly suitable as medicaments. Therefore, the present invention also provides pharmaceutical compositions which, as active material, contain at least one compound according to the present invention, optionally together with pharmaceutically-conventional carrier, adjuvant, filling and dilution agents. As active material, the pharmaceutical compositions according to the present invention preferably contain erucyl-, brassidyl- or nervonylcholine and especially preferably erucyl-phosphocholine.

The compounds according to the present invention can also be used in combination with alkylglycerols of the general formula:

(XVI)

wherein one of the substituents $R^3$ and $R^4$ is an alkyl radical containing 2 to 12 carbon atoms and the other one is a hydrogen atom. Such a pharmaceutical composition preferably contains an alkylglycerol mixture of nonyl- or octylglycerol, hexyl- or pentylglycerol and propyl- or ethylglycerol, as well as water. Such pharmaceutical composition combinations of alkylglycerols and phospholipids and the preferred contents of the individual active materials are described in DE-OS 36 41 379. The pharmaceutical compositions which contain a compound according to the present invention in combination with at least one alkylglycerol are especially suitable for topical application.

Surprisingly, the compounds according to the present invention and especially the erucyl and nervonyl derivatives do not posses any haemolytic properties such as have been observed in the case of other lysolecithins. Therefore, these compounds can be taken up in physiological solutions (for example sodium chloride solution, Ringer solution and the like) and administered intravenously. However, even more surprising is the fact that these compounds posses a distinctly better action in comparison with hexadecylphosphocholine.

The pharmaceutical compositions according to the present invention have proved to be especially suitable for combatting tumours. Thus, with erucylphosphocholine, a considerably better control in the case of tumour growth of methylnitrourea-induced mammary carcinomas is achieved in comparison with hexadecylphosphocholine administered in the same amount. Furthermore, the pharmaceutical compositions according to the present invention are suitable for combatting protozoal and fungal diseases and especially of leishmaniasis. In addition, the pharmaceutical compositions according to the present invention can also be used for the therapy of auto-immune diseases and especially of multiple sclerosis. In addition, a therapy of bone marrow diseases which have arisen due to treatment with cytostatics and other active materials which damage bone marrow is also possible.

A further subject of the present invention is also a process for the preparation of a pharmaceutical composition according to the present invention which is formulated especially as an anti-tumour agent, as agent for combatting protozoal and fungal diseases, especially leishmaniasis, as agent for the therapy of auto-immune diseases, especially multiple sclerosis, as well as an agent for the therapy of bone marrow damage.

By means of the administration of a pharmaceutical composition according to the present invention, there are provided processes for combatting tumours, protozoal and fungal diseases, anti-immune diseases and bone marrow damage. The pharmaceutical composition is thereby preferably administered intravenously. However, a subcutaneous or topical administration of the pharmaceutical composition according to the present invention is also possible.

The following Examples are given for the purpose of illustrating the present invention:

EXAMPLES

Group I: Erucyl and Brassidyl Radicals

Example 1

Erucylphosphocholine

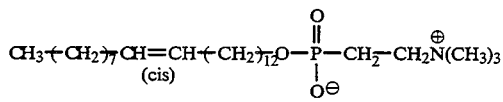

$C_{27}H_{56}NO_4P$; m.w. 489.722 calc.: C 66.22%; H 11.53%; N 2.86%; P 6.33% found: 65.98%; 11.45%; 2.69%; 6.21%

The preparation of the compounds according to Examples 1 to 19 and 33 to 35 takes place according to methods such as are described, for example, in DE 27 52 125, DE 36 41 379, DE 36 41 491, DE 36 41 377 and DE 40 13 632 or in the literature cited therein.

Example 2

Brassidylphosphocholine

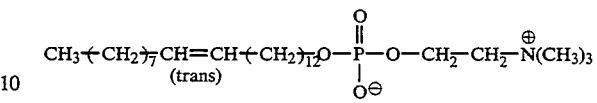

$C_{27}H_{56}NO_4P$; m.w. 489.722 calc.: C 66.22%; H 11.53%; N 2.86%; P 6.33% found: 66.04% 11.50%; 2.54%; 6.17%

Example 3

Erucylphospho-(N,N-dimethyl-N-ethyl)-ethanolamine

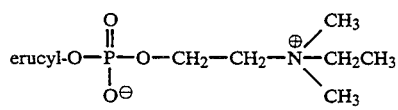

$C_{28}H_{58}NO_4P$; m.w. 503.749 calc.: C 66.76%; H 11.61%; N 2.78%; P 6.15% found: 66.51%; 11.53%; 2.69%; 2.69%; 6.01

Example 4

Brassidylphospho-(N,N-dimethyl-ethyl)-ethanolamine
$C_{28}H_{58}NO_4P$; m.w. 503.749

Example 5

Erucylphospho-(N,N-diethyl-N-methyl)-ethanolamine

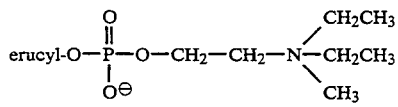

$C_{29}H_{60}NO_4P$; m.w. 517.776

Example 6

Brassidylphospho-(n,N-diethyl-N-methyl)-ethanolamine
$C_{29}H_{60}NO_4P$; m.p. 517.776

Example 7

Erucylphospho-(N,N,N-triethyl)-ethanolamine

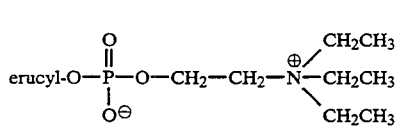

$C_{30}H_{62}NO_4P$; m.p. 531.803

Example 8

Erucylphospho-(n,N-dimethyl-N-propyl)-ethanolamine

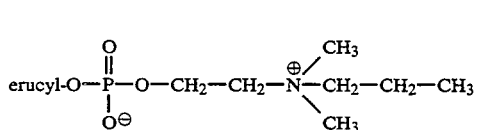

$C_{29}H_{60}NO_4P$; m.p. 517.776

Example 9

Erucylphospho-(n,N-dimethyl-N-isopropyl)-ethanolamine

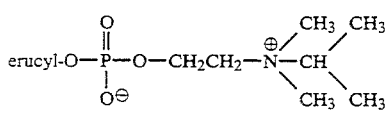

C$_{29}$H$_{60}$NO$_4$P; m.p. 517.776

Example 10

Erucylphospho-(cyclopropyl-N,N-dimethyl)-ethanolamine

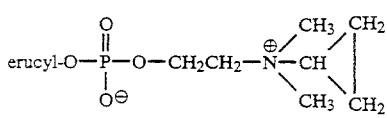

C$_{29}$H$_{58}$NO$_4$P; m.p. 515.760

Example 11

Erucylphospho-(N-allyl-N,N-dimethyl)-ethanolamine

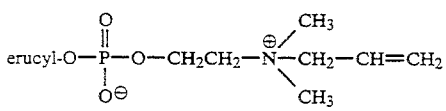

C$_{29}$H$_{58}$NO$_4$P; m.p. 515.760

Example 12

Erucylphospho-(N-ethyl-N-methyl-N-propyl)-ethanolamine

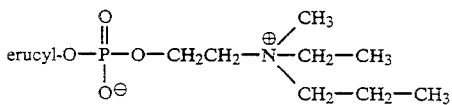

C$_{30}$H$_{62}$NO$_4$P; m.w. 531.803

Example 13

Erucylphospho-(n-butyl-N,N-dimethyl)-ethanolamine

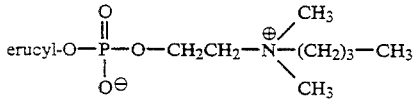

C$_{30}$H$_{62}$NO$_4$P; m.p. 530.803

Example 14

Erucylphospho-(N,N-dimethyl-N-hydroxyethyl)-ethanolamine

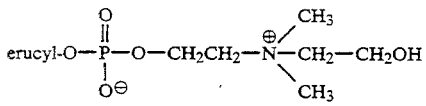

C$_{28}$H$_{58}$NO$_5$P; m.p. 519.748

Example 15

Erucylphospho-(N,N-dihydroxyethyl-N-methyl)-ethanolamine

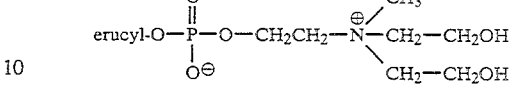

C$_{29}$H$_{60}$NO$_6$P; m.p. 549.774

Example 16

Erucylphospho-(N-cyclobutyl-N,N-dimethyl)-ethanolamine

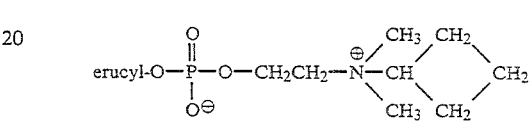

C$_{30}$H$_{60}$NO$_4$P; m.w. 529.787

Example 17

Erucylphosphoric acid N-methylpyrrolidinoethyl ester

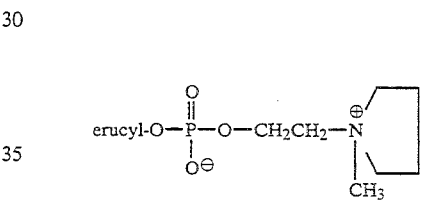

C$_{29}$H$_{58}$NO$_4$P; m.p. 515.760

Example 18

Erucylphosphoric acid N-ethylpyrrolidinoethyl ester

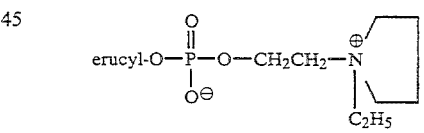

C$_{30}$H$_{60}$NO$_4$P; m.w. 529.787

Example 19

Erucylphosphoric acid N-methylmorpholinoethyl ester

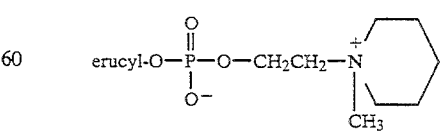

C$_{30}$H$_{60}$NO$_4$P; m.w. 529.787

Example 20

1-Erucyl-2-methyl-rac-glycero-3-phosphocholine

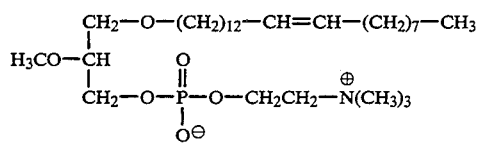

$C_{31}H_{64}NO_6P$; m.w. 577.828

The preparation of the compounds according to Examples 20 to 22 and 27 to 32 takes place, for example, as described in DE 32 39 817 or in the literature cited therein or as described in Example 1.

Example 21

1-Erucyl-2-methyl-sn-glycero-3-phosphocholine

Example 22

3-Erucyl-2-methyl-sn-glycero-1-phosphocholine

All modifications with regard to the amino group, as well as the exchange of the erucyl radical for the brassidyl radical, can be transferred to the base structure 1-erucyl-2-methylglycerol with the same methodology and with comparable yields.

Example 23

1-Erucylmercapto-2-methoxymethylpropyl-2'-(N,N,N-trimethyl)-ammonioethyl phosphate

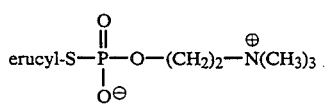

$C_{32}H_{66}NO_5PS$; m.w. 607.916 calc.: C 63.23%; H 10.94%; N 2.30%; P 5.10% found: 62.95%; 10.89%; 2.26%; 4.98%

The sulphur-containing compounds can be prepared according to the method of Bosies et al. (Lipids, 22, 947–951/1987). However, the corresponding thiols are phosphorylated according to the methods of phosphorylation cited in Example 1 and further reacted.

Here, too, the modifications of 1 to 19 can be introduced, starting from the appropriate alcohol.

Example 24

1-Erucylmercapto-2-methoxymethylpropyl-2'-(N,N-dihydroxyethyl-N-methyl)-ammonioethyl phosphate
$C_{34}H_{70}NO_7PS$; m.w. 667.968

Example 25

Furthermore, according to the method of Houlihan et al. (Lipids, 22, 884–890/1987), the following active materials, which contain erucyl or brassidyl radicals, can be prepared which are build up on the following base structure: (±)-2-{hydroxy-[tetrahydro-2-(alkyl)-methylfuran-2-yl]-methoxyphosphinyl-oxy}-N,N,N-trimethylethaniminium hydroxide. The alcohol as base structure is, however, phosphorylated according to the methods cited in Example II and further reacted.

Erucyl as alkyl radical; $C_{32}H_{64}NO_6P$; m.w. 589.839

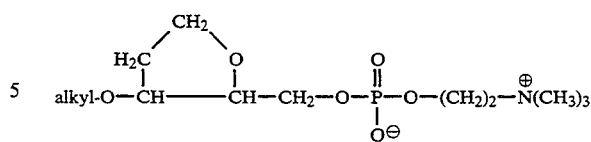

Example 26

Brassidyl as alkyl radical; $C_{32}H_{64}NO_6P$; m.w. 589.839.

Example 27

1-Erucyl-3-methyl-rac-glycero-3-phosphocholine

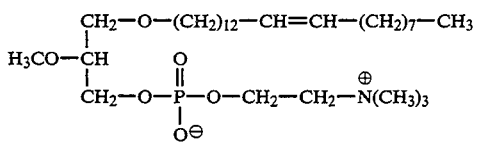

$C_{31}H_{64}NO_6P$; m.w. 577.828 calc.: C64.44%; H 11.17%; N 2.42%; P5.36 found: 64.29%; 11.11%; 2.39%; 5.31%

Example 28

1-Erucyl-3-methyl-sn-glycero-3-phosphocholine

Example 29

3-Erucyl-1-methyl-sn-glycero-2-phosphocholine

Example 30

1-Erucylpropane-1,2-diol phosphocholine

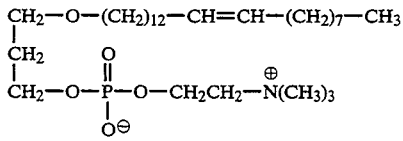

$C_{30}H_{62}NO_5P$; m.w. 547.802 calc.: C 65.78%; H 11.41%; N 2.56%; P 5.65% found: 65.61%; 11.35%; 2.49% 5.58%

Example 31

1-Erucylpropane-1,2-diol phosphocholine
$C_{30}H_{62}NO_5P$; m.w. 547.802

Example 32

Erucylglycol phosphocholine

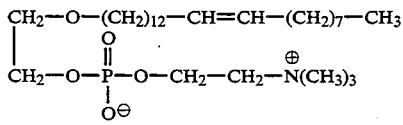

$C_{29}H_{60}NO_5P$; m.w. 533.775 calc.: C 65.26%; H 11.33%; N 2.62%; P 5.80% found: 65.17% 11.26% 2.57% 5.72%

Group II: Nervonyl radicals

All compounds of Group I (Example 1 to 32) can also be prepared by analogous processes with nervonyl radicals.

Example 33

Nervonyl phosphocholine (cis-15-tetracosenyl-phosphocholine)

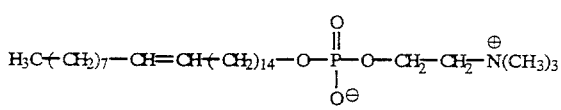

$C_{29}H_{60}NO_4P$; m.w. 517.776 calc.: $C_{67.27}\%$; H 11.68%; N 2.71%; P 5.98% found: 67.13% 11.59% 2.64% 5.68%

Example 34

Nervonylphospho-(N,N-dimethyl-N-ethyl)-ethanolamine

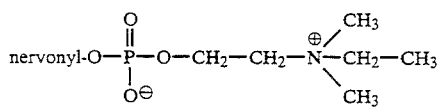

$C_{30}H_{62}NO_4P$; m.w. 531.803

Example 35

Nervonylphospho-(N,N-diethyl-N-methyl)-ethanolamine

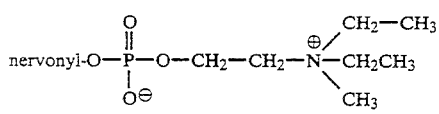

$C_{31}H_{64}NO_4P$; m.w. 545.830

Nervonyl derivatives which are analogous to the compounds according to Examples 7 to 26 are prepared according to the there-described processes.

Example of use

The preparation of a hexadecylphosphocholine formulation in liposomes takes place according to DE 40 26 136.0. 12 mmol hexadecylphosphocholine, 15 mmol cholesterol and 3 mmol DPPG are dissolved in 200 ml propan-2-ol with warming. The solvent is then stripped off in a vacuum and the fine-divided lipid film is mixed with 300 ml phosphate buffer solution (pH 7.0). Subsequently, the mixture is maintained at 40° C. for 60 minutes while slowly rotating.

Subsequently, the lipid suspension obtained is transferred into the pressure cell of a French press and pressed out at 740 MPa and this procedure is repeated three times. The liposome dispersion formed is then centrifuged for 30 minutes at 27000 g and 5° C. and the supernatant recovered.

At the same time, a erucylphosphocholine formulation is prepared in physiological sodium chloride solution.

Methylnitrourea-induced mammary carcinomas in the rat are treated with the formulation prepared in the above-described manner in an amount which corresponds to the given concentrations of hexadecylphosphocholine or erucylphosphocholine per kg of rat as daily dosage. After 4 weeks, the tumour weight of untreated control animals is taken as being 100%. This value corresponds to unhindered tumour growth. The tumour animals in the treated group achieved values of from 0 to 100% in comparison with the control group, as is given in the following Table:

TABLE

| active material | formulation | amount/day | action[+] |
|---|---|---|---|
| hexadecylphosphocholine | liposomes | 30 μmol | <10% |
| | | 10 μmol | −90% |
| erucylphosphocholine | in physiol. NaCl sol. | 10 μmol | <10% |
| | | 6 μmol | <10% |
| | | 3 μmol | <10% |

[+]residual weight of the tumour in %, referred to the untreated control.

I claim:

1. Compounds of the formula:

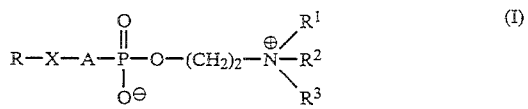

wherein R is selected from the group consisting of an erucyl, a brassidyl and a nervonyl radical, $R^1$, $R_2$, and $R_3$ are independently straight-chained, branched or cyclic saturated or unsaturated alkyl radicals containing up to 4 carbon atoms, which optionally contains a hydroxyl group, and wherein two of the alkyl radicals which are $R_1$, $R_2$, and $R_3$ can be connected to form a ring, A is a valency bond or a radical of one of the following formulas:

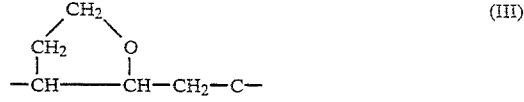

wherein the radicals of the formulas (II) to (VI) have an orientation such that the oxygen atom is attached to the phosphorus atom of compound (I), and X is an oxygen or sulfur atom.

2. The compound according to claim 1, wherein $R_1$, $R_2$, and $R_3$ independently contain or lack a hydroxyl group.

3. The compound according to claim 1, wherein X is an oxygen and A is a valency bond.

4. The compound according to claim 1, wherein X is an oxygen or sulfur atom and A is a radical of one of the following formulas:

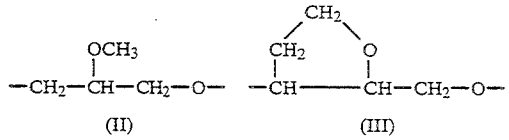

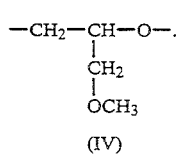

5. The compound according to claim 1, wherein $R^1$, $R^2$, and $R^3$ are methyl radicals.

6. The compound according to claim 1, wherein the compound is erucylphosphocholine.

7. A pharmaceutical composition comprising the compound of claim 1 as an active ingredient together with a pharmaceutically conventional carrier, adjuvant, filler and dilution agent.

8. The pharmaceutical composition according to claim 7 wherein the active ingredient is selected from the group consisting of erucyl-, brassidyl- and nervonyl-phosphocholine.

9. The pharmaceutical composition according to claim 8, wherein erucylphosphocholine is the active ingredient.

10. The pharmaceutical composition according to claim 7 wherein the active ingredient is contained in a physiological solution.

11. The pharmaceutical composition according to claim 7, further comprising at least one alkylglycerol of the formula:

wherein either $R^5$ or $R^6$ is an alkyl radical containing 2–12 carbon atoms and the other is a hydrogen atom.

12. The pharmaceutical composition according to claim 11, wherein a mixture of nonyl- or octylglycerol, hexyl- or pentylglycerol and propyl- or ethylglycerol and water are present in the composition.

* * * * *